United States Patent [19]

Kripke et al.

[11] Patent Number: 5,302,389
[45] Date of Patent: Apr. 12, 1994

[54] METHOD FOR TREATING UV-INDUCED SUPPRESSION OF CONTACT HYPERSENSITIVITY BY ADMINISTRATION OF T4 ENDONUCLEASE

[75] Inventors: Margaret L. Kripke, Kingwood, Tex.; Daniel B. Yarosh, Merrick, N.Y.

[73] Assignee: Board of Regents, The University of Texas System, Austin, Tex.

[21] Appl. No.: 931,218

[22] Filed: Aug. 17, 1992

[51] Int. Cl.$^5$ .................. A61K 37/22; A61K 37/54
[52] U.S. Cl. ................... 424/94.6; 424/94.3; 424/450
[58] Field of Search ............... 424/94.3, 94.6, 450

[56] References Cited

U.S. PATENT DOCUMENTS 4,959,205  9/1990  Brunner et al. ............... 424/59
5,077,211  12/1991  Yarosh ........................ 435/193

FOREIGN PATENT DOCUMENTS

WO90/00598  1/1990  PCT Int'l Appl. .

OTHER PUBLICATIONS

Kripke, M. L. et al., "Effect of T4N5 Liposome-Enhanced DNA Repair on UV-Induced Immune Suppression in the Mouse," S/pm-D6, *Photochemistry & Photobiology*, 53:Suppl., Apr. 1991, p. 295.
Yarosh, D. B. et al., "T4N5 Liposomes Reduce UV Mutagenesis in Mammalian Cells by Increasing Dimer Repiar and Reducing the Patch Size," S/pm-D7, *Photochemistry & Photobiology*, 53:Suppl., Apr. 1991, p. 295.
Kripke, M. L. et al.; Proc. Natl. Acad. Sci. USA 89:7516-7520 (Aug. 15, 1992).
Kripke, M. L. et al.; J. Invest. Dermatol. 86:543-549 (1986).
Applegate, L. A. et al.: Identification of the Molecular Target for the Suppression of Contact Hypersensitivity by Ultraviolet Radiation. J. Exp. Med. 170:1117-1131 (1989).
Yarosh, D. et al.: Pyrimidine Dimer Removal Enhanced by DNA Repair Liposomes Reduces the Incidence of UV Skin Cancer in Mice, Cancer Research 52:4227-4231 (Aug. 1, 1992).

*Primary Examiner*—Robert A. Wax
*Assistant Examiner*—Eric Grimes
*Attorney, Agent, or Firm*—Arnold, White & Durkee

[57] ABSTRACT

Exposing the skin to UV radiation interferes with the induction of the T-cell mediated immune response, including both delayed (DHS) and contact (CHS) hypersensitivity immune responses initiated at non-irradiated sites. The present inventors have discovered that DNA is at least one of the targets for UV-induced hypersensitivity, and demonstrate that the application of DNA repair enzymes can reverse the damaging effects of UV irradiation on both the DHS and CHS response. The usefulness of the invention in this regard was tested using a model immunosuppression system in mice. In these studies, mice were first exposed to UV radiation and then liposomes were used to deliver a dimer-specific excision repair enzyme to their epidermis in situ. The application of liposomal T4 endonuclease V encapsulated to the UV-irradiated skin both decreased the number of cyclobutane pyrimidine dimers in the epidermis and prevented suppression of both delayed and contact hypersensitivity responses. Moreover, the formation of suppressor lymphoid cells was inhibited. These studies illustrate that the delivery of lesion-specific DNA repair enzymes to living skin after UV irradiation is an effective tool for restoring immune function and suggest that this approach may be broadly applicable to preventing other alterations caused by DNA damage, including preventing or reversing viral activation (e.g., herpes virus activation), oncogene expression, or autoimmune episodes.

6 Claims, 3 Drawing Sheets

METHOD FOR TREATING UV-INDUCED SUPPRESSION OF CONTACT HYPERSENSITIVITY BY ADMINISTRATION OF T4 ENDONUCLEASE

The government owns an interest in the present invention pursuant to NIH grants R5 ES04075, R01-CA52457, R44-CA52401, and CA-16672.

BACKGROUND OF THE INVENTION

1. Field of the Invention

The present invention relates generally to methods for the treatment or prevention of UV-induced immunosuppression. More particularly, the invention relates to the treatment of UV-induced immunosuppression of the contact hypersensitivity type (CHS), through the application of liposome-encapsulated DNA repair enzymes.

2. Description of the Related Art

Wavelengths of UV radiation in the middle, or UV-B (280-320 nm), range can impair a variety of immune responses in humans and laboratory animals both locally, within UV-irradiated skin, and systemically, at distant sites (1). Exposure of mice to UV-B radiation interferes with the rejection of UV-induced skin cancers and the induction of delayed and contact hypersensitivity (DHS, CHS) responses initiated at unirradiated sites; these forms of immune suppression are associated with the induction of antigen-specific suppressor T lymphocytes (2). How UV-B radiation exerts its systemic, immunosuppressive effects is a question of considerable interest, both for understanding the regulatory pathways governing these immune responses and for assessing the potential effects of UV-B radiation on human health. The DHS response is particularly important in this regard because this T-lymphocyte-mediated immune reaction is responsible for protection against many chronic infectious diseases.

Current experimental evidence implicates soluble substances derived from UV-irradiated keratinocytes as the probable mediators of UV-induced systemic suppression of DHS and CHS responses (3-5). However, the initial photobiological reaction responsible for triggering the cascade of events leading to activation of the suppressor pathway of the immune response remains controversial. Based on an in vivo action spectrum for systemic suppression of CHS in the mouse, it has been proposed that urocanic acid, a deamination product of histidine, present in the stratum corneum, is the photoreceptor for this form of UV-induced immunosuppression (6). Several subsequent studies supported this hypothesis (7-9) by demonstrating that the cis isomer of urocanic acid, which is formed upon UV irradiation of the native molecule, has immunosuppressive activity in mice.

On the other hand, studies using the South American opossum Monodelphis domestica implicated DNA damage as the initiating event in UV-induced suppression of CHS, at least in these distant relatives of eutherian mammals (10). Cells from these marsupials have the ability to repair UV-induced pyrimidine dimers in DNA by means of a photoreactivating enzyme, which binds to DNA, forming a complex that absorbs energy in he visible wavelength range. The absorbed energy splits the dimers, thereby restoring the DNA to its original configuration. In these studies, UV-induced suppression of CHS was prevented by exposing the opossums to photoreactivating light immediately after exposure to UV radiation (10). These results implicated DNA damage as the trigger for UV-induced suppression of CHS in marsupials; however, its role in immune suppression in placental mammals remained open to question. Because cells in the skin of adult mice do not have a photoreactivation mechanism for repairing pyrimidine dimers (11), this approach could not be used to determine the role of DNA damage in UV-induced immunological effects in the mouse.

The present inventors have devised an alternative approach for examining the role of DNA damage in the initiation of UV-induced immunosuppression in mice by using liposomes containing an excision repair enzyme, T4 endonuclease V, which is specific for pyrimidine dimers (12). When topically applied to murine skin, T4N5 liposomes penetrate cells of the epidermis (13, unpublished results). The multilamellar lipid vesicles destabilize at low pH, thereby delivering the endonuclease intracellularly and increasing the rate of repair of pyrimidine dimers in DNA (14,15).

The preparation and use of liposome encapsulated DNA repair enzymes in the treatment of certain diseases and conditions related to UV irradiation, including xeroderma pigmentosum and certain cancers, has been described (see, e.g., Yarosh, U.S. Pat. No. 5,077,211 and PCT application publication number WO 90/00598, published Jan. 25, 1990, both incorporated herein by reference). However, previously there has been no indication that the damage to DNA caused by UV irradiation was related to immunosuppression. Thus, there was no reason to believe that therapies directed to DNA repair would have an effect upon reversing or ameliorating UV-induced immunosuppression. The present invention surprisingly provides a basis for this conclusion.

In particular, the present invention presents studies wherein the inventors have analyzed the role of pyrimidine dimers, induced in DNA by UV irradiation in vivo, in initiating systemic suppression of the DHS and CHS responses. The results of these studies demonstrate the usefulness of liposome-encapsulated DNA repair enzymes in the treatment of both systemic immunosuppression of the DHS as well as the CHS response. Accordingly, the present invention expands our previous understanding of the causal relationship between UV irradiation, DNA repair and cancer, to demonstrate a relationship between DNA repair and reversal of UV-mediated immunosuppression.

SUMMARY OF THE INVENTION

The present invention therefore arises from the inventors' discovery that liposome-encapsulated DNA repair enzymes such as liposomal T4N5 endonuclease can be employed to treat and/or prevent, and thereby ameliorate, the immunosuppressive effects of UV irradiation, particularly the T-cell mediated response, including reversing or ameliorating the suppression of both the CHS and DHS immune responses.

T4N5 liposomes of the present invention will most advantageously be administered epicutaneously, for example, at sites that will receive or have received immunosuppressive amounts of UV irradiation, but the use of these liposomes parenterally should not be ruled out. When used epicutaneously, the liposomes are applied to the affected area in an effective amount, typically following suspension in a convenient topical vehicle, such as a suspension in 1% hydrogel.

The amount of T4N5 liposomes applied to the skin will generally depend upon the concentration of liposomal suspension, and will be apparent to those of skill in the art in light of the examples set forth below. Generally speaking, preferred liposomal suspensions will have from about 0.25 to about 0.75 μg/ml T4 endonuclease V. The preparation of preferred liposomes is described below, as well as in significant detail in U.S. Pat. No. 5,077,211 and PCT publication WO 90/00598.

From the surprising findings set forth herein, that DNA damage plays some role in UV-induced immunosuppression, it is believed that still further advantages and applications will be realized through the use of T4N5 liposomes. For example, it is now known that UV-mediated immunosuppression correlates with the release of various cytokines, such as tumor necrosis factor alpha (TNFa) and interleukin 10 (IL-10). Interleukin 10 is known to play a role in and of itself in causing immunosuppression of both the DHS and CHS response. The inventors propose that much of the T-cell mediated immunosuppression observed following UV radiation is the result of the release of cytokines such as these by T cells. The inventors further propose that the ability of T4N5 liposomes to lead to a lessening of the T-cell mediated immune suppression is a function of the enzyme's ability to reduce cytokine release by T cells.

The mechanism by which DNA repair enzymes would effect a reduction in cytokine release is not known, but is currently the subject of investigation by the inventors. Regardless of the mechanism, however, it is proposed that T4N5 liposomes will be useful in moderating the release or action of cytokines such as these in their immunosuppressive action.

It is also known that UV radiation leads to the activation of certain viruses, such as herpes virus. It may be the case that UV radiation plays a role in the activation of oncogenic viruses, as well as in the activation of certain autoimmune diseases such as lupus. Importantly, suppression of the T-cell mediated immune response likely plays a role in each of these various conditions. Assuming this to be the case, the inventors propose that the T4N5 liposomes of the present invention will prove to be useful in the treatment or prevention of viral triggering events such as UV induced herpes or oncogene activation, and even in the treatment or prevention of autoimmune episodes.

In still further embodiments, the inventors propose that the use of sunscreens in combination with T4N5 liposomes will provide even further advantages in accordance with the invention. A particular advantage to the use of both T4N5 liposomes together with sunscreens is proposed based on the inventors premise that the sunscreen will have an effect in preventing direct DNA damage, whereas the T4N5 liposomes will have a more direct effect on the immunosuppressive action of UV radiation. The combination, therefore, should prove particularly useful.

DETAILED DESCRIPTION OF THE PREFERRED EMBODIMENTS

Figure 1A:
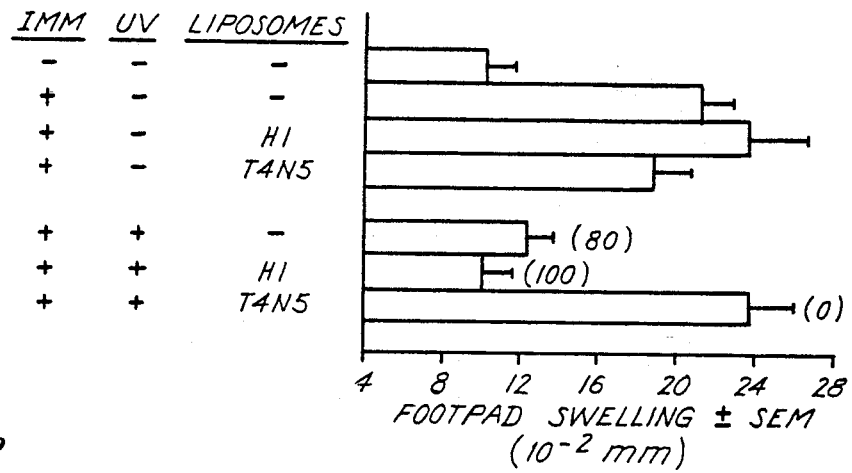
FIG. 1A and 1B. Effect of T4N5 liposomes on suppression of induction of DHS to Candida. C3H mice were exposed to 5 kJ/m$^2$ UV-B radiation. Liposomes containing T4 endonuclease V (T4N5) or heat-inactivated (HI) endonuclease were applied to UV-irradiated skin immediately thereafter. On day 3, mice were immunized s.c. at an unirradiated site with $2 \times 10^7$ C. albicans (IMM). All mice were challenged 9 days later by footpad injection of Candida antigen; footpad swelling was measured 24 hr later. (A) Numbers in parenthesis = % suppression, calculated using formula 1, relative to the appropriate control group (e.g., for test group treated with HI liposomes after UV irradiation, positive control was that treated with HI liposomes without UV, etc.). (B). Spleen cells from these mice were injected i.v. into normal recipients, which were immediately immunized with C. albicans; recipients were challenged 9 days later. Numbers in parenthesis = % suppression calculated using formula I, relative to positive control group (mice immunized but not injected with spleen cells).

The following examples illustrate techniques discovered by the inventors for the treatment of immunosuppression, particularly immunosuppression of the CHS type, through the use of liposome encapsulated DNA repair enzymes such as T4 endonuclease V. It should be appreciated by those of skill in the art that the techniques disclosed in the examples which follow represent laboratory techniques that are illustrative in their design. The presentation of these studies are believed to be readily applicable to the use of such compositions in the clinic for the treatment and/or prevention of UV immunosuppression.

EXAMPLE I

1. MATERIALS AND METHODS a. Mice

Specific-pathogen-free C3H/HeN(mammary tumor virus negative) female mice were obtained from the Frederick Cancer Research Facility Animal Production Area (Frederick, Md.). Age-matched mice between 10 and 12 wk old were used for each experiment. They were housed in filter-protected cages, and ambient lighting was controlled to provide 12-h light - 12-h dark cycles. Autoclaved National Institutes of Health open formula mouse chow and water were provided ad libitum. The animal facility is accredited by the AAALAC, and all procedures were approved by the Institutional Animal Care and Use Committee.

b. UV Irradiation

The UV source was a bank of six FS40 sunlamps (National Biological Corp., Twinsburg, Ohio), which emit approximately 60% of their radiation within the UV-B (280–320 nm) range and have a peak emission at 313 nm. The average irradiance of the source was approximately 9 $W/m^2$, as measured by an IL-700 radiometer (International Light, Inc., Newburyport, Mass.) equipped with a PT171C UV-B 320 filter, and an A127 quartz diffuser, which detects radiation in the wavelength range between 280 and 320 nm. The dose-rate of the incident radiation received by animals was 4.5 $W/m^2$ because of screening by the cage lid. Before irradiation, the dorsal fur of the mice was shaved with electric clippers, and the animals were placed in individual compartments in cages that were located 20 cm below the light source. Mice used for measuring CHS had their ears covered with electrical tape during irradiation. Except for exposure to UV radiation, control mice were treated exactly the same as the irradiated mice.

c. T4N5 Liposomes

T4N5 liposomes were prepared by encapsulating purified, recombinant T4 endonuclease V in liposomes composed of phosphatidylcholine, phosphatidylethanolamine, oleic acid, and cholesterol hemisuccinate (2:2:1:5 molar ratio) by the detergent dialysis method (14). The concentration of the entrapped enzyme was determined by ELISA (16) and is expressed as mg T4 endonuclease V per ml of vehicle. The encapsulated activity was assayed by nicking of UV-supercoiled DNA with and without dissolution of the liposomes (16). Control preparations of liposomes contained boiled (enzymatically inactive) T4 endonuclease V (14). The liposomes were mixed into a 1% hydrogel (Hypan SS201, Kingston Hydrogels, Dayton, N.J.) made with phosphate-buffered saline and applied to shaved mouse skin with a moist cotton swab. Immediately after UV irradiation, 0.25 ml of liposome suspension containing 0.5 mg/ml T4 endonuclease V was applied to the UV-irradiated skin of each mouse.

d. Assay for Pyrimidine Dimers

The number of pyrimidine dimers in epidermal DNA was measured by the endonuclease-sensitive site assay using alkaline agarose gels (17). In this assay, the frequency of dimers in DNA is measured by the change in average single-stranded DNA length in alkaline gels after treatment with T4 endonuclease V. The lengths of DNA in the control and endonuclease-digested samples are calculated using DNA restriction fragments of defined length, run in adjacent lanes of the gel, and the average molecular length is computed by the same (weight - average molecular weight)/2 calculation used in the well-established alkaline sucrose gradient method (18). Under these conditions, dimer induction is directly proportional to UV-B fluence up to 100 dimers per million bases (17), and all measurements reported here are within this range. The dimer measurements in the alkaline agarose gel assay agree closely with results from the alkaline sucrose gradient method (18), confirming the accuracy of this technique.

The epidermis was isolated by overnight digestion of excised dorsal skin in 0.25% trypsin on ice, and the DNA was purified by two rounds of proteinase K digestion (100 mg/ml in 1% SDS, 37° C. for 30 min); phenol, phenol/chloroform (1:1 v/v), and chloroform extraction; and ethanol precipitation. The DNA was then treated with purified T4 endonuclease V (10 mg/ml) to produce breaks at all dimer sites, and the single strands were separated by alkaline agarose gel electrophoresis. Photographic negatives of the ethidium-bromide stained gels were scanned by a Hoefer GS300 scanning densitometer, and the output was digitized by a Data Translations 2805 analog/digital converting board in a Compaq Deskpro computer. The stored files were used to calculate the average molecular length for each sample, and the change in average molecular length was used to calculate the dimer frequency. The approximation of linear film response was used to calculate average molecular length because the T4 endonuclease V-treated samples showed fluorescence that fell within the linear portion of the film response curve; the untreated DNA samples showed fluorescence of single high molecular weight bands, most affected by a non-linear film response, but nearly identical in all samples and subject to the same small error. At each UV dose, the average dimer number per unit length of DNA from at least two samples were compared in skin treated with either active or inactive liposomes or not treated with liposomes.

e. DHS Response

Formalin-fixed *Candida albicans* was prepared as described previously (19). Mice were sensitized by injecting 0.1 ml of formalin-fixed *C. albicans* cells ($1 \times 10^7$) s.c. into each flank. Nine days later, the hind footpad thickness was measured with a spring-loaded micrometer (Swiss Precision Instruments, Los Angeles, Calif.), and the animals were challenged by intradermal injection of 50 ml of candida antigen (Antigen Supply House, Northridge, Calif.) in both hind footpads. Footpad thickness was measured again 24 hr later, and the swelling was determined by subtracting prechallenge from postchallenge measurements. The thickness of the footpads before challenge ranged from 1.7 to 2.0 mm. For both DHS and CHS, % suppression was calculated from formula I as follows:

$$\% \text{ Suppression} = 1 - \frac{T-N}{P-N} \times 100, \quad \text{[Formula 1]}$$

where N=negative control (response of unsensitized mice to challenge); P=positive control (response of sensitized mice ± liposomes to challenge); T=test group (response of mice given UV±liposomes before sensitization and challenge).

f. CHS Response

Animals were sensitized by the epicutaneous application of 2,4-dinitrofluorobenzene (DNFB) (50 ml of a 0.3% v/v solution in acetone) on shaved abdominal skin. Five days later, the mice were challenged by applying 5 ml of a 0.2% solution of DNFB onto each ear surface. Alternatively, mice were sensitized with fluorescein isothiocyanate (FITC), according to the method of Thomas et al. (20). A 0.5% FITC solution (Aldrich Chemicals, Milwaukee, Wis.) was prepared in a solvent composed of equal volumes of acetone and dibutyl phthalate (Aldrich). For sensitization, 0.4 ml of the solution was applied to shaved abdominal skin. Five days later, the CHS reaction was elicited by applying 5 ml of the 0.5% FITC solution to each surface of both ears. The thickness of each ear was measured with a micrometer immediately before challenge and 24 hr later. The ear thickness before challenge ranged from 0.24 to 0.30 mm.

g. Transfer of Spleen Cells

On day 10 after sensitization (day 6 for CHS), spleens were removed from mice that exhibited a decreased DHS or CHS response and from appropriate control animals. Single-cell suspensions were prepared from pooled spleens by teasing the spleens apart in Hanks' balanced salt solution. Clumps were removed by filtration through nylon mesh. The cells were washed once and refiltered, and $10^8$ viable, nucleated cells were injected i.v. into syngeneic recipients. Immediately thereafter, the recipients were sensitized with *C. albicans* or FITC; the DHS or CHS response was measured 10 or 6 days later, respectively, as described above, and % suppression was calculated according to formula 1.

h. Statistical Analysis

The significance of differences in the DHS or CHS response between control and treatment groups was determined using an ANOVA for repeated measures. Each group contained at least five mice, and each experiment was performed at least twice and usually three times.

2. RESULTS a. Effect of T4N5 Liposomes on UV-induced Suppression of the Induction of DHS to Candida Exposure of mice to UV-B radiation before immunization inhibits the induction of the DHS response to *C. albicans* injected s.c. at an unirradiated site; this treatment also causes the formation of suppressor T lymphocytes that suppress the induction of DHS to Candida (19). To determine whether liposomes containing T4 endonuclease V would abrogate these immunosuppressive effects of UV irradiation, groups of mice were exposed to a single dose of 5 $kJ/m^2$ UV-B radiation, and liposomes containing active (T4N5) or heat-inactivated (HI) enzyme were immediately applied to the UV-irradiated dorsal skin. The mice were immunized 3 days later by s.c. injection of formalin-fixed Candida.

Figure 1B:
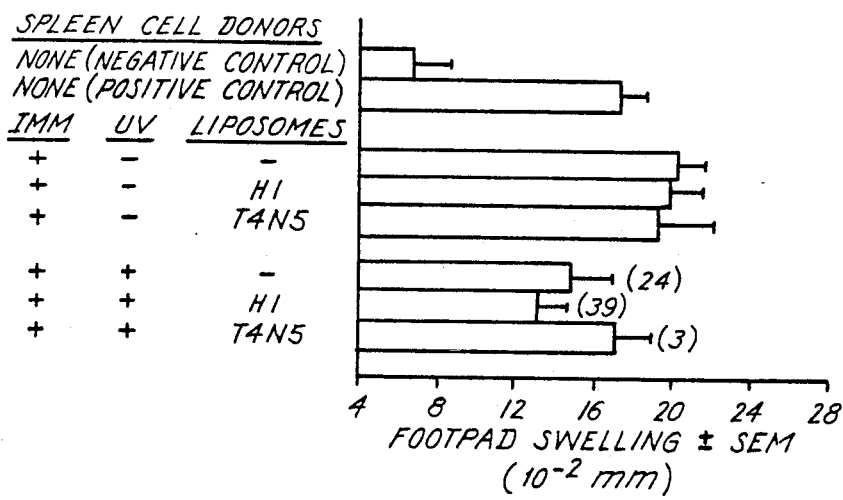

As shown in FIG. 1A, application of T4N5 liposomes completely abrogated the suppressive effect of UV irradiation; in contrast, liposomes containing heat-inactivated endonuclease had no effect. This experiment was performed six times with very similar results. Transfer of spleen cells from the immunized, UV-irradiated mice to normal, syngeneic recipients rendered the recipients unresponsive to immunization with Candida, indicating that suppressor cells were present in the spleen cell suspension (FIG. 1B). Treatment of the spleen cell donors with T4N5 liposomes after UV irradiation prevented the development of suppressor cells; transfer of spleen cells from these animals to normal mice did not affect the magnitude of their DHS response to Candida.

It is conceivable that the T4N5 liposomes could be blocking the release or action of the immunosuppressive mediators produced by UV-irradiated cells (3–5) or activating an immunostimulatory mechanism, rather than acting at the level of DNA repair. To test these possibilities, control experiments were performed in which the T4N5 liposomes were applied to ventral, unirradiated skin or were applied to dorsal, UV-irradiated skin 2 days after UV treatment. Application of T4N5 liposomes on ventral (unirradiated) skin had no effect on UV-induced suppression of the DHS response: 51% suppression in mice treated on ventral skin with T4N5 liposomes versus 57% in UV-irradiated mice and 50% in mice treated on ventral skin with liposomes containing heat-inactivated enzyme.

In a second experiment, mice were exposed to UV radiation and T4N5 liposomes were applied immediately or 2 days after UV; all groups were immunized with Candida 5 days after UV. As before, applying T4N5 liposomes immediately after UV irradiation completely restored the DHS response (0% suppression). In contrast, applying the active liposomes 2 days after UV had no effect on UV-induced suppression (68%) compared with mice given UV alone (68% suppression) or given inactive liposomes immediately (70% suppression) or 2 days after UV irradiation (72% suppression).

b. UV Dose-response

Figure 3:
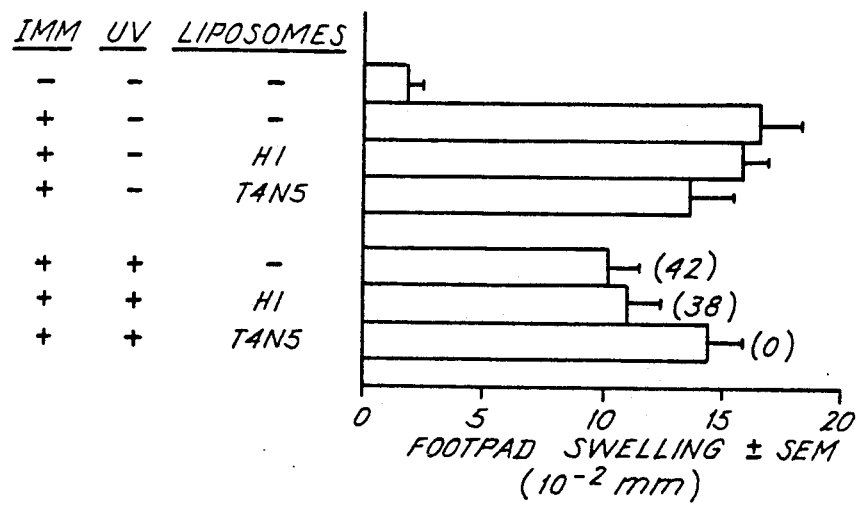
FIG. 3. Effect of T4N5 liposomes on suppression of elicitation of DHS to Candida. C3H mice were immunized with C. albicans s.c.; 5 days later they were exposed to 10 kJ/m$^2$ UV-B radiation and treated with liposomes containing T4 endonuclease V (T4N5) or heat-inactivated (HI) enzyme. On day 6 they were challenged in the footpad with Candida antigen; footpad swelling was measured 24 hr. later. Numbers in parenthesis = % suppression (calculated using formula 1) relative to appropriate control group (see legend to FIG. 1 and methods section of Example I).
Figure 2:
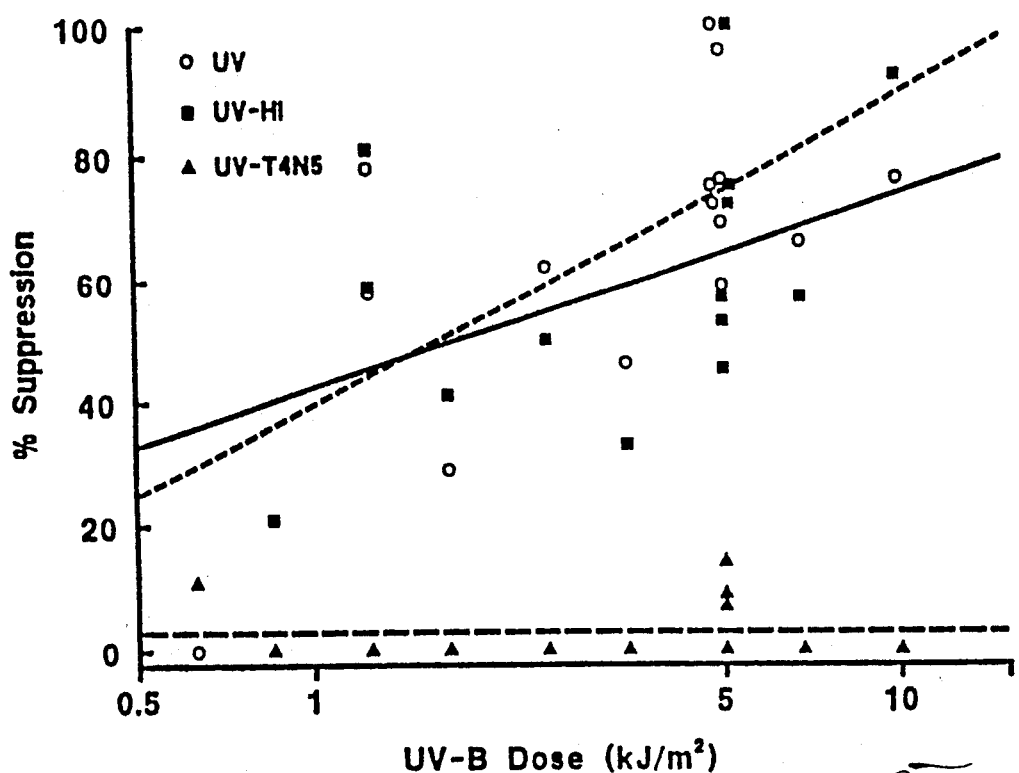
FIG. 2. UV dose-response for suppression of DHS: Effect of T4N5 and inactive liposomes. Data are the pooled results from eight separate experiments; results are expressed as UV dose (log scale) versus % suppression of DHS to Candida (calculated using formula 1), relative to appropriate control groups (see legend to FIG. 1 and Materials and Methods for details). Each data point is calculated from the mean footpad swelling of 5 test and 5 control mice. Lines were obtained by linear regression analysis. (UV—, UV-HI—, UV-T4N5—).

It is also possible that at different doses of UV radiation, different mechanisms might be involved in immunosuppression. We therefore performed a dose-response study to determine whether liposome treatment would completely restore the DHS response across a wide range of UV doses. As illustrated in FIG. 2, the T4N5 liposomes abrogated the UV-induced suppression of DHS at all doses of UV radiation tested. In contrast, the response of mice treated with liposomes containing heat-inactivated endo-nuclease did not differ significantly from that of mice given UV irradiation without liposomes as determined by linear regression analysis.

c. Effect of T4N5 Liposomes on UV-induced Inhibition of the Elicitation of DHS to Candida Previous studies demonstrated that exposing mice to UV radiation after immunization also reduces the DHS response; however, higher doses of UV radiation are required, and suppressor lymphocytes do not seem to be involved. To determine whether T4N5 liposomes would also prevent this form of UV-induced immunosuppression, experiments were performed in which mice were treated with UV radiation and liposomes 5 days after immunization. As shown in FIG. 3, treatment with T4N5 liposomes, but not liposomes containing heat-inactivated enzyme, completely abrogated the inhibitory effect of UV radiation on elicitation of the DHS response.

d. Effect of T4N5 Liposomes on UV-induced Suppression of the Induction of CHS It has been postulated (6) that UV-induced systemic suppression of CHS in the mouse is mediated by urocanic acid, which, when it absorbs UV radiation, undergoes a trans-to-cis isomerization. If this hypothesis were correct, an increase in the repair of UV-induced pyrimidine dimers in DNA should not abrogate UV-induced suppression of CHS. To test this possibility, we examined the effect of T4N5 liposomes on UV-induced suppression of the induction of CHS to DNFB. Mice were exposed to a single dose of 10 $kJ/m^2$ UV-B radiation on shaved dorsal skin. Three days later, they were sensitized by application of DNFB onto shaved ventral skin. Some groups of mice were treated with T4N5 liposomes or liposomes containing heat-inactivated endonuclease on UV-irradiated skin immediately after irradiation; unirradiated control groups were also treated with both liposome preparations.

Figure 4A:
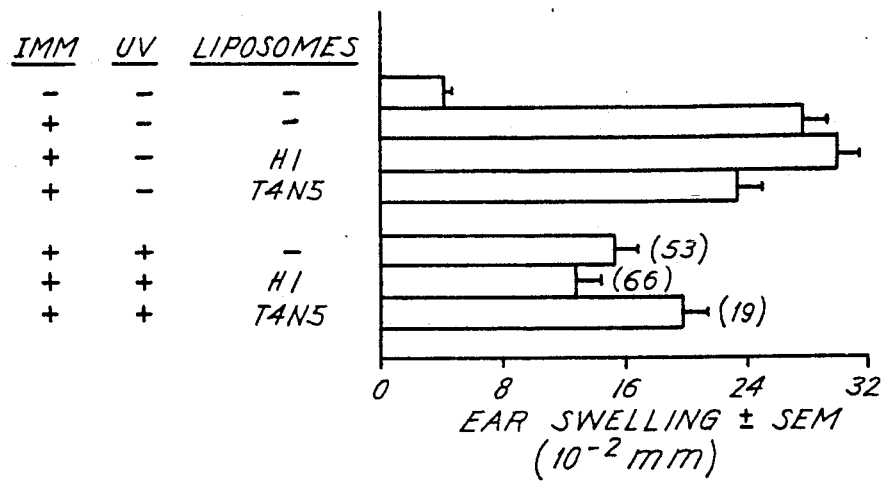
FIG. 4A-4C. Effect of T4N5 liposomes on UV-induced suppression of the induction of CHS. C3H mice were exposed to 10 kJ/m$^2$ UV-B radiation on shaved dorsal skin and immediately treated with liposomes containing T4 endonuclease V (T4N5) or heat-inactivated (HI) enzyme. Three days later, they were painted with 2,4-dinitrofluorobenzene (DNFB) or fluorescein isothiocuanate (FITC) on shaved ventral skin. Five days after immunization, they were challenged with the same hapten on the ears; ear swelling was measured 24 hr later. Numbers in parenthesis = % suppression (calculated using formula 1) relative to the appropriate control group (A & B; see legend to FIG. 1 and Materials and Methods for details). Spleen cells from mice in the experiment shown in FIG. 4B were transferred to normal recipients i.v., which were immediately immunized by epicutaneous application of FITC. Recipients were challenged 5 days later; ear swelling was measured 24 hr after challenge. Numbers in parenthesis = % suppression relative to the positive control group (C).

As shown in FIG. 4A, treatment of UV-irradiated mice with active liposomes significantly increased the CHS response to nearly the level observed in unirradiated, T4N5 liposome-treated animals ($P=0.027$ for UV,T4N5 group vs. UV,HI group; $P=0.036$ for UV,T4N5 group vs. UV group), but the response was not completely restored ($P=0.04$ for UV,T4N5 group vs. non-irradiated, T4N5 group).

Figure 4B:
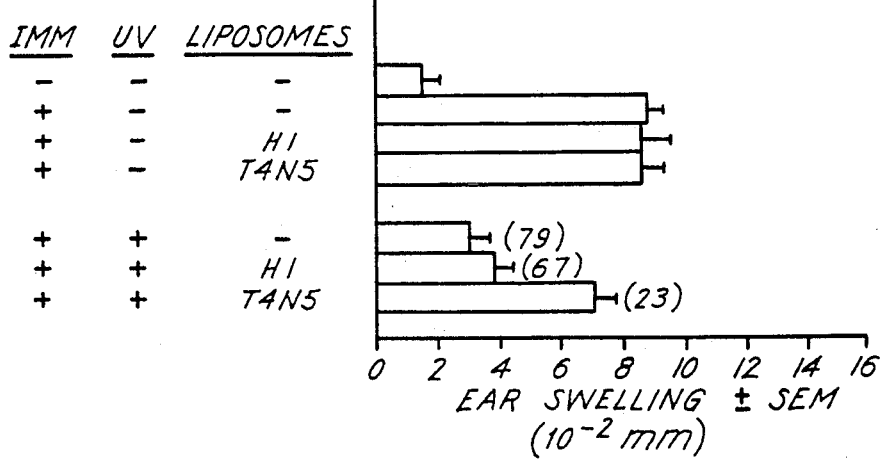
Figure 4C:
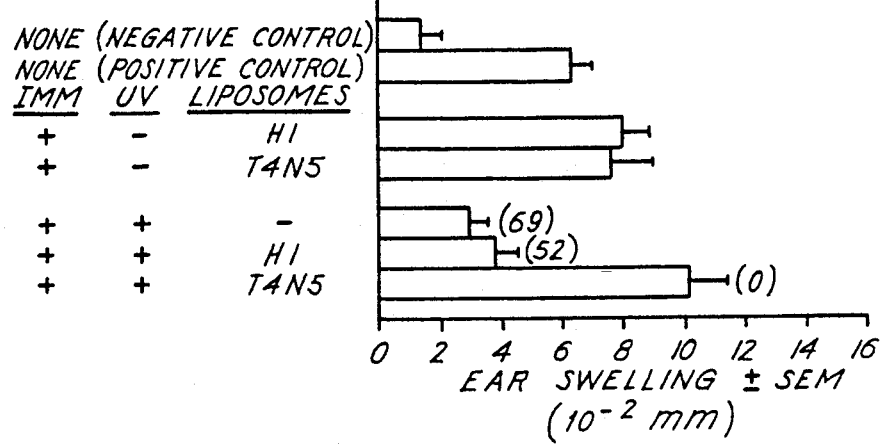

In a similar study using FITC as a contact sensitizer, the CHS response was also increased in UV-irradiated, T4N5-treated mice, but not completely restored; however, the difference between the UV, T4N5-treated group and the nonirradiated, T4N5-treated group was not statistically significant (FIG. 4B). Transfer of spleen cells from the UV-irradiated, FITC-sensitized mice to normal, syngeneic recipients confirmed the presence of suppressor cells that inhibited the induction of CHS to FITC; such suppressor cells could not be detected in mice given T4N5 liposomes immediately after UV irradiation (FIG. 4C).

e. Effect of T4N5 Liposomes on the Number of Pyrimidine Dimers

Figure 5:
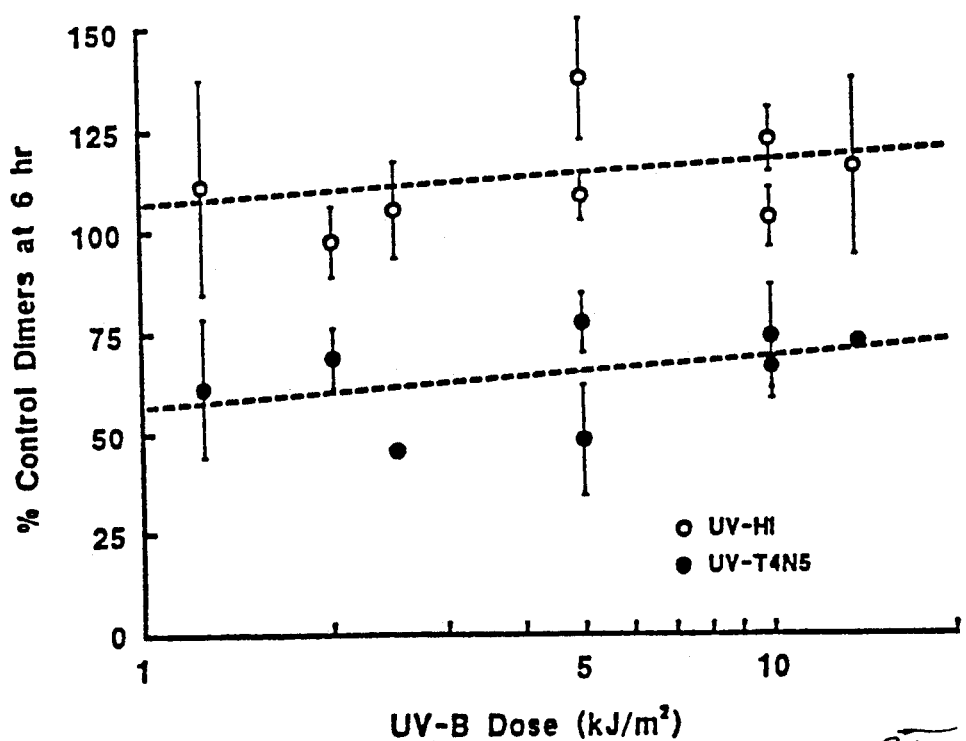
FIG. 5. Repair of pyrimidine dimers in mouse skin treated with T4N5 liposomes. Some C3H mice from the experiments depicted in FIG. 2 were killed 6 hr after UV-B irradiation and DNA from the epidermis was analyzed for pyrimidine dimers by the endonuclease-sensitive-site assay. Dimer frequency is plotted versus UV dose on a log scale. The dimer frequency in epidermal DNA from UV-irradiated, control mice was compared to that from UV-irradiated mice treated with active (T4N5) (6) or inactive (HI) (0) liposomes. Each point represents the average of two to six measurements ± standard error of the mean, and the lines were obtained by linear regression analysis.

T4N5 liposomes were shown previously to reduce the number of pyrimidine dimers in DNA isolated from the epidermis of UV-irradiated hairless mice (14). These animals have an endogenous DNA repair mechanism that removes up to 40% of the cyclobutane pyrimidine dimers from epidermal DNA during the first 6 hr after UV irradiation (17), and T4N5 liposomes reduce the number remaining by an additional 40% during that time period (14). To ensure that the liposomes were also increasing the repair of such lesions in the epidermis of the inbred C3H mice used in these experiments, pyrimidine dimers were measured at 6 hr after UV irradiation in mice taken at random from treatment groups of the experiments depicted in FIG. 2. The pooled results of these measurements are presented in FIG. 5. The number of pyrimidine dimers per $10^6$ bases was directly proportional to the UV dose ($11\pm1$ dimers/$10^6$ bases/$kJ/m^2$ UV-B; $r=0.986$), and is expressed as a percentage of the dimers in epidermal DNA from mice treated with UV radiation only. Dimers in the epidermis of mice treated with inactive liposomes ranged from 97 to 135% of that in the control animals; in contrast, dimers in the epidermis of mice treated with T4N5 liposomes ranged from 44 to 74% of the control values across the range of UV doses tested. These results demonstrate that at 6 hr after UV irradiation, fewer pyrimidine dimers were present in the epidermis of mice treated with T4N5 liposomes than in untreated mice or mice treated with inactive liposomes.

3. DISCUSSION

Based on these studies, the inventors conclude that UV-induced suppression of the DHS response to Candida in C3H mice is triggered entirely by the DNA-damaging effects of UV radiation. Other possible explanations for the effect of the T4N5 liposomes were ruled out by using control liposome preparations containing heat-inactivated endonuclease and by performing control experiments in which liposomes were applied to unirradiated skin or were applied 2 days after UV irradiation. Because the endonuclease used to repair DNA damage is highly specific for pyrimidine dimers, these lesions are the most likely initiators of this immunosuppressive effect of UV irradiation. Regardless of the specific DNA lesion involved, however, the initiation of suppression of the DHS response by UV can be accounted for entirely by DNA damage, and there is no evidence that other molecules altered by UV radiation, such as urocanic acid, can by themselves trigger photoimmunosuppression.

Systemic suppression of CHS in the mouse following exposure to UV-B radiation is thought to involve different mechanisms than suppression of DHS (21). Our studies indicated, however, that systemic suppression of the CHS response in UV-irradiated C3H mice was also mediated mainly by DNA damage in the form of pyrimidine dimers. Unlike the studies with DHS, suppression of the CHS response could not be restored completely by treatment with liposomes. A small component of the suppression, comprising 10 to 25%, was not reversed by treatment with T4N5 liposomes, suggesting that an additional mechanism contributes to UV-induced systemic suppression of the CHS response.

One question raised by the foregoing studies is why the T4N5 liposomes cause complete, or nearly complete restoration of immunological function, while they appear in FIG. 4 to repair only around 40 to 50% of the pyrimidine dimers remaining in epidermal DNA. Most likely, this is due to the fact that in the studies depicted in FIG. 4, dimers were measured 6 hr after UV irradiation, whereas immunization occurred 3 days later. In these studies, DNA repair measurements were made at this early time point to avoid the complication introduced by subsequent UV-induced epidermal hyperplasia. However, an experiment in hairless mice was performed under the same conditions of UV irradiation, in which dimers were measured in DNA pre-labeled with $^3H$-thymidine in vivo. This study demonstrated that repair of 80% of the dimers occurred over a 30-hr period after exposure to 5 $kJ/m^2$ UV-B radiation (D. Yarosh, unpublished data), confirming that complete excision repair of dimers occurs slowly, over a period of days. Alternatively, target DNA involved in UV-induced immunosuppression may be repaired more rapidly than other DNA regions, since it is known that actively transcribed DNA is repaired preferentially after UV irradiation (22).

The foregoing studies demonstrated that skin treated with active T4N5 liposomes exhibited repair of about 50% of the remaining dimers, over a wide range of UV-B doses. This result is puzzling because one would expect a larger proportion of the dimers to be repaired at the lower UV-B doses where fewer dimers are induced. Perhaps not all regions of the genome are equally accessible to T4 endonuclease V; alternatively, some other factor released or activated in proportion to the UV dose (e.g., a DNA ligase or helicase) may become rate limiting after T4 endonuclease V has incised all the remaining dimers.

These studies are consistent with those carried out in the opossum, which demonstrated by means of photoreactivation that DNA damage in the skin, and particularly pyrimidine dimers, are primarily responsible for generating systemic suppression of CHS (10). The target cell of the UV irradiation has not been identified; however, the keratinocyte seems to be the most likely candidate. These cells produce a variety of cytokines involved in immune and inflammatory reactions (23), and they release immunosuppressive mediators after exposure to UV radiation in vitro (3–5). Therefore, the inventors propose that UV-induced damage to the DNA of keratinocytes triggers the synthesis and release of the immunosuppressive cytokines that inhibit the DHS and CHS responses and cause the induction of suppressor T lymphocytes.

The studies also demonstrate that the use of liposomes to deliver lesion-specific DNA repair enzymes to the epidermis in situ provides an effective means of preventing UV-induced immunosuppression. In principle, this approach could be applied to the study of other biological endpoints induced by DNA damage and may have practical applications in preventing pathological effects resulting from damage to DNA.

REFERENCES

The following references are hereby incorporated herein by reference to the extent that they explain, teach or provide a basis for materials and methodology disclosed herein.

1. Parrish, J. A., Kripke, M. L. & Morison W. L. (1983) Photoimmunology, eds. Parrish, Kripke, Morison, Plenum Publishing Corporation, New York.
2. Kripke, M. L. (1984) Immunol. Rev. 80, 87–102.
3. Schwarz, T., Urbanska, A., Gschnait, F. & Luger, T. A. (1986) J. Invest. Dermatol. 87, 289–291.
4. Kim, T-Y., Kripke, M. L. & Ullrich, S. E. (1990) J. Invest. Dermatol. 94, 26–32.
5. Ullrich, S. E., McIntyre, B. W. & Rivas, J. M. (1990) J. Immunol. 145, 489–498.
6. DeFabo, E. C. & Noonan, F. P. (1983) J. Exp. Med. 157, 84–98.
7. Ross, J. A., Howie, S. E. M., Norval, M. & Maingay, J. P. (1987) J. Invest. Dermatol. 89, 230–233.
8. Harriott-Smith, T. G. & Halliday, W. J. (1988) Clin. Exp. Immunol. 72, 174–177.
9. Norval, M., Gilmour, J. W. & Simpson, T. J. (1990) Photodermatol, Photoimmunol. Photomed. 7, 243–248.
10. Applegate, L. A., Ley, R. D., Alcalay, J. & Kripke, M. L. (1989) J. Exp. Med. 170, 1117–1131.
11. Ananthaswamy, H. & Fisher, M. S. (1981) Cancer Res. 41, 1829–1833.
12. Gordon, L. & Haseltine, W. (1980) J. Biol. Chem. 255, 12047–12050.
13. Yarosh, D. (1992) in Liposome Dermatics (eds. Braun-Falco, O., Korting, H. and Maibach, H.) Springer-Verlag (in press).
14. Yarosh, D. B., Tsimis, J. & Yee, V. (1990) J. Soc. Cosmet. Chem. 41, 85–92.
15. Yarosh, D. B., Kibitel, J., Green, L. & Spinowitz, A. (1991) J. Invest. Dermatol. 97, 147–150.
16. Ceccoli, J., Rosales, N., Tsimis, J. & Yarosh, D. B. (1989) J. Invest. Dermatol. 93, 190–194.
17. Yarosh, D. & Yee, V. (1990) J. Photochem. Photodiol. 7, 173–179.
18. Freeman, S., Blackett, B., Moneteleone, D., Setlow, R., Sutherland, B. & Sutherland, J. (1986) Anal. Biochem. 158, 119–129.
19. Denkins, Y., Fidler, I. J. & Kripke, M. L. (1989) Photochem. Photobiol. 49, 615–619.
20. Thomas, W. R., Edwards, A. J., Watkins, M. C. & Asherson, G. L. (1980). Immunol. 39, 21–27.
21. Kripke, M. L. & Morison, W. L. (1986) J. Invest. Dermatol. 86, 543–549
22. Bohr, V., Okumoto, D. & Hanawalt, P. (1986) Proc. Natl. Acad. Sci. USA 83, 3830–3833.
23. Luger, T. A. & Schwarz T. (1990) J. Invest. Dermatol. 95, 100s–104s.

What is claimed is:

1. A method for the treatment of UV induced suppression of the T-cell mediated immune response in a human individual comprising topically administering to the individual a therapeutically effective amount of liposome encapsulated T4 endonuclease V (T4N5) DNA repair enzyme.

2. The method of claim 1, further comprising topical administration of a sunscreen agent.

3. A method for the treatment of UV induced suppression of the contact hypersensitivity type immune response in a human individual comprising topically administering to the individual a therapeutically effective amount of liposome encapsulated T4 endonuclease V (T4N5) DNA repair enzyme.

4. The method of claim 1 or 3, wherein the liposome comprises phosphatidylcholine, phosphatidylethanolamine, oleic acid and cholesterol.

5. The method of claim 1 or 3 wherein the liposomes are administered as a liposome suspension comprising about 0.5 mg/ml T4N5 enzyme.

6. The method of claim 1 or 3, wherein the liposomes are comprised in a hydrogel suspension.

* * * * *